(12) United States Patent
Shirai et al.

(10) Patent No.: US 10,765,349 B2
(45) Date of Patent: Sep. 8, 2020

(54) MAGNETIC RESONANCE IMAGING DEVICE AND METHOD FOR CALCULATING OXYGEN EXTRACTION FRACTIONS

(71) Applicant: Hitachi, Ltd., Chiyoda-ku, Tokyo (JP)

(72) Inventors: Toru Shirai, Tokyo (JP); Ryota Satoh, Tokyo (JP); Yo Taniguchi, Tokyo (JP); Hisaaki Ochi, Tokyo (JP); Yoshihisa Sotome, Tokyo (JP); Yoshitaka Bito, Tokyo (JP); Takenori Murase, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/342,612

(22) PCT Filed: Oct. 11, 2017

(86) PCT No.: PCT/JP2017/036826
§ 371 (c)(1),
(2) Date: Apr. 17, 2019

(87) PCT Pub. No.: WO2018/083952
PCT Pub. Date: May 11, 2018

(65) Prior Publication Data
US 2019/0261906 A1    Aug. 29, 2019

(30) Foreign Application Priority Data
Nov. 7, 2016    (JP) ................................. 2016-217307

(51) Int. Cl.
*A61B 5/145*      (2006.01)
*G01R 33/50*      (2006.01)
(Continued)

(52) U.S. Cl.
CPC ........ *A61B 5/14542* (2013.01); *A61B 5/0042* (2013.01); *A61B 5/055* (2013.01);
(Continued)

(58) Field of Classification Search
CPC ... A61B 5/14542; A61B 5/0042; A61B 5/055; A61B 5/14551; G06T 1/00;
(Continued)

(56) References Cited

U.S. PATENT DOCUMENTS

| 8,958,866 B2 * | 2/2015 | Bolar ..................... A61B 5/055 |
| | | 324/309 |
| 10,010,277 B2 * | 7/2018 | Carp .................. A61B 5/14551 |
| (Continued) | | |

FOREIGN PATENT DOCUMENTS

JP    2015-62637 A    4/2015

OTHER PUBLICATIONS

Translation of the International Preliminary Report on Patentability issued in corresponding International Application No. PCT/JP2017/036826 dated May 16, 2019.
(Continued)

*Primary Examiner* — G. M. A Hyder
(74) *Attorney, Agent, or Firm* — Foley & Lardner LLP

(57) ABSTRACT

Provided is a technique for calculating an oxygen extraction fraction by using MRI where the oxygen extraction fraction in a brain including brain parenchyma is calculated via a simple processing without an impact on an examinee, such as administration of caffeine. For this purpose, an MRI apparatus of the present invention measures a complex image of nuclear magnetic resonance signals, and calculates from thus measured complex image, a physical property distribution for obtaining a physical property image reflecting the oxygen extraction fraction. Then, thus calculated physical property distribution is separated into tissue-specific physical property distributions for at least two tissues (separated tissue images). After converting any of the separated tissue images into the oxygen extraction fraction, a distribution of the oxygen extraction fraction is estimated based on the condition that a value of any selected pixel is substantially equal to a mean value of pixels surrounding the selected pixel.

13 Claims, 11 Drawing Sheets

(51) Int. Cl.
| | |
|---|---|
| A61B 5/00 | (2006.01) |
| A61B 5/055 | (2006.01) |
| G01R 33/44 | (2006.01) |
| G01R 33/54 | (2006.01) |
| G01R 33/56 | (2006.01) |
| G06T 1/00 | (2006.01) |
| G01N 24/08 | (2006.01) |

(52) U.S. Cl.
CPC ......... *G01R 33/443* (2013.01); *G01R 33/543* (2013.01); *G01R 33/5602* (2013.01); *G01R 33/5608* (2013.01); *G06T 1/00* (2013.01); *G01N 24/08* (2013.01)

(58) Field of Classification Search
CPC ............... G01R 33/443; G01R 33/543; G01R 33/5602; G01R 33/5608; G01R 33/4824; G01R 33/5617; G01R 33/5616; G01R 33/50; G01N 24/08
See application file for complete search history.

(56) References Cited

U.S. PATENT DOCUMENTS

| | | | |
|---|---|---|---|
| 2014/0219533 A1* | 8/2014 | Sato | G06T 11/008 382/131 |
| 2015/0084628 A1 | 3/2015 | Sato | |

OTHER PUBLICATIONS

Translation of the International Preliminary Report on Patentability issued in corresponding International Application No. PCT/JP2017/036826 dated Oct. 11, 2017.

Audrey P. Fan et al., "Quantitative Oxygenation Venography from MRI Phase", Magnetic Resonance in Medicine, 2014, vol. 72, 149-159.

Jingwei Zhang et al., "Quantitative Mapping of Cerebral Metabolic Rate of Oxygen (CMRO2) Using Quantitative Susceptibility Mapping (QSM)", Magnetic Resonance in Medicine, 2015, vol. 74, 945-952.

Jan Sedlacik et al., "Validation of Quantitative Estimation of Tissue Oxygen Extraction Fraction and Deoxygenated Blood Volume Fraction in Phantom and In Vivo Experiments by Using MRI", Magnetic Resonance in Medicine, 2010, vol. 63, 910-921.

Xiang He et al., " Quantitative BOLD: Mapping of Human Cerebral Deoxygenated Blood Volume and Oxygen Extraction Fraction: Default State", Magnetic Resonance in Medicine, 2007, ,vol. 57, 115-126.

Bolar, D. S. et al., Quantitative Physiology/Imaging of Oxygenation, ISMRM, 23, Institute of Navigation, 2015.

Zhang, J., et al., High Resolution Cerebral Metabolic Rate of Oxygen [CMRO2] using Quantitative Susceptibility Mapping (QSM) and an Oxygen Extraction Fraction (OEF) Constraint, ISMRM, 23, Institute of Navigation, 2015, #3940.

Dimov, A. et al., Estimation of Blood Oxygenation using Quantitative Susceptibility Mapping, ISMRM, 23, Institute of Navigation, 2015, #1703.

McDaniel, P. et al., Improved Accuracy in Susceptibility-based OEF Measurements by Mitigation of Partial-Volume Effects via Combined Magnitude and Phase Reconstruction, ISMRM, 23, Institute of Navigation, 2015, #3330.

International Search Report with English translation and Written Opinion issued in corresponding application No. PCT/JP2017/036826 dated Dec. 19, 2017.

* cited by examiner

1A

100

1B

120

1C

130

3A

3B

PARTICULATE SUBSTANCE EXTRACTION A

LINEAR SUBSTANCE EXTRACTION B

8A

8B

8C

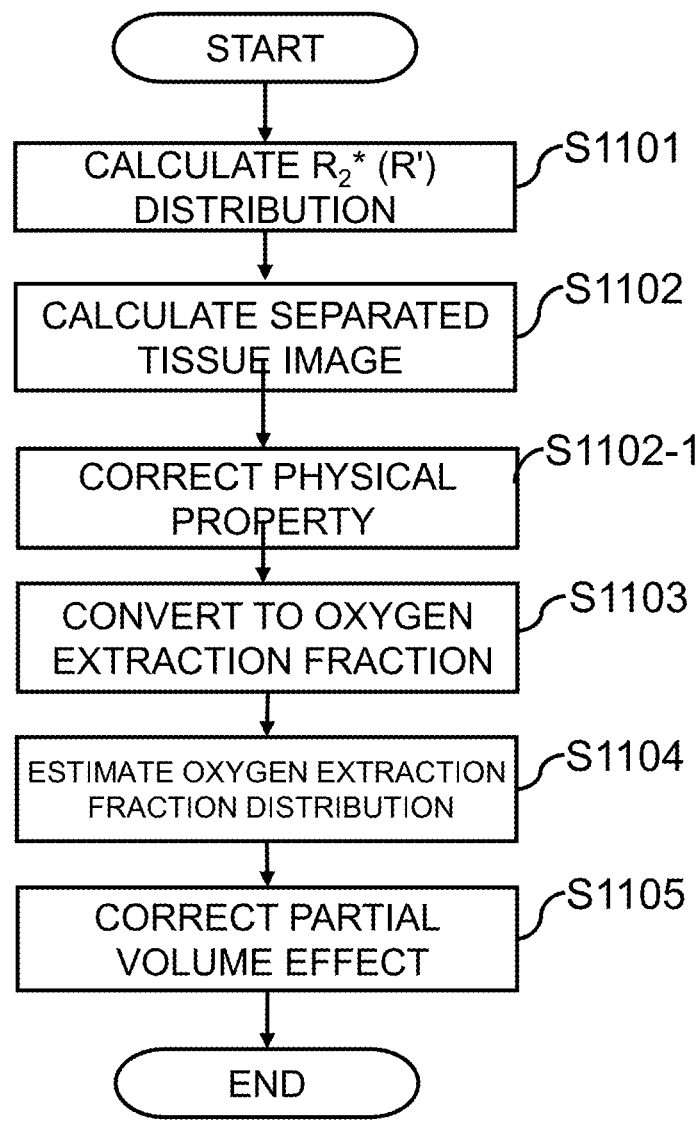

MAGNETIC RESONANCE IMAGING DEVICE AND METHOD FOR CALCULATING OXYGEN EXTRACTION FRACTIONS

TECHNICAL FIELD

The present invention relates to a magnetic resonance imaging (MRI) technique. More particularly, the present invention relates to an image processing technique for calculating oxygen content characteristics of a living body, by using an acquired image.

BACKGROUND ART

A magnetic resonance imaging apparatus is a non-invasive medical diagnostic imaging apparatus utilizing a nuclear magnetic resonance phenomenon that a hydrogen nucleus (proton) placed in a static magnetic field resonates with an RF magnetic field at a specific frequency. Since a nuclear magnetic resonance signal varies according to various physical properties such as proton density and relaxation time, there is a possibility that metabolism of a living tissue and blood perfusion are evaluated, in addition to evaluation of lesion morphology and physical evaluation. Currently, such utilization of the nuclear magnetic resonance signal is applied to evaluation of cerebral ischemia disease and tumor, and attempts are being made to predict a treatment effect and a prognosis.

In order to determine the state of cerebral ischemia disease and tumor, and a degree of severity thereof, it is clinically important to evaluate oxygen metabolism in tissues according to oxygen imaging, such as brain oxygen extraction fraction (OEF: Oxygen Extraction Fraction) and oxygen saturation ($StO_2$: Tissue Oxygen Saturation) in tumor. Currently used clinical evaluation of oxygen metabolism sets as a gold standard, Positron Emission Tomography (PET) examination that employs $^{15}O$-labeled gas and $^{18}F$ labeled fluoromisonidazole (FMISO) agent. However, the PET examination causes problems that the time of examination is long and there is exposure to radiation. On the other hand, an MRI examination features that the examination time is short and there is no exposure to radiation, allowing reduction of impacts on a patient.

There have been suggested several methods for calculating the oxygen extraction fraction by using MRI. As one of the methods, a velocity-selective pre-pulse sequence and a spin-echo sequence are used to measure blood signals in capillaries of the living tissue at a plurality of TEs. Based on the measured signal strength at the plurality of TEs, a value of T2 of the blood signal is calculated by signal fitting. Then, by the use of the relationship between the oxygen saturation of the blood obtained separately and the T2 value of the blood signal, the oxygen extraction fraction in the living tissue is calculated (e.g., see the Patent Document 1).

As alternatives, there are methods to calculate the oxygen extraction fraction from magnetic susceptibility variations in a living body. As one of those methods, there is a method that uses quantitative susceptibility mapping (QSM) to capture a variation in magnetic susceptibility reflecting the oxygen extraction fraction. The QSM is a method of calculating local magnetic field variations caused by a susceptibility difference between tissues, from a phase distribution in an MR image, and estimating a susceptibility distribution, on the basis of a relational expression between the magnetic field and the magnetic susceptibility.

When oxygen is consumed in the living tissue, oxyhemoglobin in arterial blood changes to deoxyhemoglobin in venous blood. It is known that the magnetic susceptibility of the venous blood varies linearly with respect to the concentration of deoxyhemoglobin in the venous blood. Therefore, according to the QSM method, the oxygen extraction fraction in the living tissue can be calculated according to the variation of magnetic susceptibility of deoxyhemoglobin.

For example, one of the methods for calculating the oxygen extraction fraction according to the QSM is focusing only on the susceptibility distribution in veins calculated by the QSM method, and calculating the oxygen saturation in veins based on the magnetic susceptibility (e.g., Non Patent Document 1). In another method, caffeine is administered to an examinee, and cerebral blood flow (CBF) and the susceptibility distribution are calculated by using the ASL (Arterial Spin Labeling) and the QSM method, respectively, before and after the administration of caffeine. Then, the OEF is calculated before or after the administration of caffeine, under the condition that the metabolic rate of oxygen ($CMRO_2$) represented by a product of CBF and OEF does not change before and after the administration of caffeine (e.g., see Non Patent Document 2).

PRIOR ART DOCUMENT

Patent Document

Patent Document 1
DESCRIPTION of U.S. Pat. No. 8,958,866

Non Patent Document

Non Patent Document 1
Audrey P. Fan, et al., "Quantitative Oxygenation Venography from MRI Phase", Magnetic Resonance in Medicine, 2014, vol. 72, pp. 149-159
Non Patent Document 2
Jingwei Zhang, et al., "Quantitative Mapping of Cerebral Metabolic Rate of Oxygen ($CMRO_2$) Using Quantitative Susceptibility Mapping (QSM)", Magnetic Resonance in Medicine, 2015, vol. 74, pp. 945-952

DISCLOSURE OF THE INVENTION

Problems to be Solved by the Invention

According to the method disclosed in the Patent Document 1, T2 value of the blood signal in the capillaries of the living tissue is calculated, and there is an advantage that the oxygen extraction fraction in brain parenchyma can be calculated. However, the T2 value of blood varies non-linearly with respect to a blood composition such as a hematocrit value, and therefore, there is a problem that it is difficult to calculate the oxygen extraction fraction based on the T2 value of blood.

The method disclosed by the Non Patent Document 1 uses the QSM method to calculate the oxygen extraction fraction from the venous susceptibility, and thus, this method has an advantage of high accuracy. However, according to this method, only the oxygen extraction fraction in venous blood is calculated, and there is a problem that the oxygen extraction fraction in brain parenchyma cannot be calculated.

Even though the method disclosed by the Non Patent Document 2 is advantageous in that calculation of the oxygen extraction fraction in the brain parenchyma is possible by using the QSM method, there is a problem that administration of caffeine has an impact on an examinee. In addition, there is also a problem that accuracy of the calculated oxygen extraction fraction is likely to be reduced, for a disease showing a change of $CMRO_2$ before and after the administration of caffeine.

The present invention has been made in view of the problems above, and an object of the present invention is to provide a technique for calculating the oxygen extraction fraction (OEF) in the brain including brain parenchyma, according to a simple processing without any impact such as caffeine administration, in calculating the OEF that utilizes an image obtained by MRI.

Means for Solving the Problems

The present invention calculates a physical property image from a complex image generated from nuclear magnetic resonance signals, using as a pixel value, a physical property reflecting oxygen content characteristics, such as an oxygen extraction fraction. Then, thus calculated physical property image is separated into images of at least two types of tissue, and any of this separated tissue images is converted into oxygen content characteristics. Thereafter, on the basis of a condition that a value of any pixel is substantially equal to a mean value of the surrounding pixels, a distribution of the oxygen content characteristics in a target area is estimated.

Specifically, an MRI apparatus of the present invention comprises a measuring unit having a transmitter configured to transmit an RF magnetic field pulse to a subject placed in a static magnetic field, a receiver configured to receive a nuclear magnetic resonance signal generated from the subject, and a gradient magnetic field generator configured to provide the static magnetic field with a gradient magnetic field, a measurement controller configured to control an operation of the measuring unit, according to an imaging sequence being preset, and a computer configured to perform computation on the nuclear magnetic resonance signal being received, wherein, the computer comprises an image reconstructor configured to generate a complex image from the nuclear magnetic resonance signal acquired at least one echo time, a physical property distribution calculator configured to calculate a physical property image, having as a pixel value, a physical property reflecting oxygen content characteristics, a tissue separator configured to separate the physical property image of a target area, into images for at least two types of tissue to generate a plurality of separated tissue images, an oxygen content characteristics converter configured to convert the physical property of each pixel into oxygen content characteristics, as to any of the plurality of separated tissue images, and an oxygen content characteristics distribution estimator configured to estimate a distribution of the oxygen content characteristics in the target area, based on a condition that a value of any pixel is equal to a mean value of surrounding pixels, in the separated tissue image after converting the pixel value into the oxygen content characteristics. The oxygen content characteristics include either of the oxygen extraction fraction and oxygen saturation.

Advantage of the Invention

In calculating the oxygen content characteristics by using MRI, a distribution of the oxygen content characteristics in the brain including brain parenchyma can be calculated according to the simple processing, without an impact on the subject, such as the administration of caffeine, thereby enhancing diagnostic accuracy.

BRIEF DESCRIPTION OF THE DRAWINGS

FIG. 11 is a flowchart showing the process for calculating the distribution of the oxygen extraction fraction according to a third embodiment.

BEST MODE FOR CARRYING OUT THE INVENTION

Embodiments of an MRI apparatus to which the present invention is applied will now be described.

[Overview of MRI Apparatus]

Figure 1:
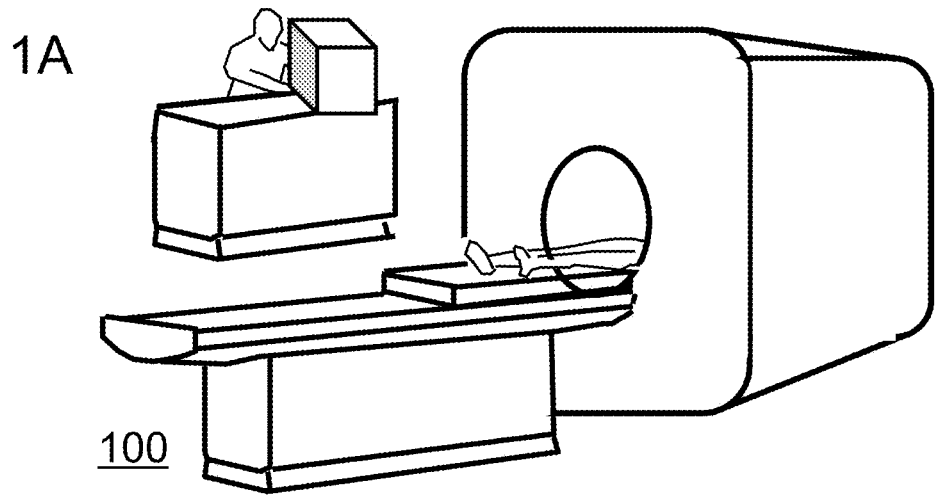
FIG. 1A is an external view of a vertical magnetic resonance imaging (MRI) apparatus according to an embodiment of the present invention.
FIG. 1B is an external view of a horizontal MRI apparatus according to an embodiment of the present invention.
FIG. 1C is an external view of the MRI apparatus with enhanced sense of openness according to an embodiment of the present invention.
Figure 1:
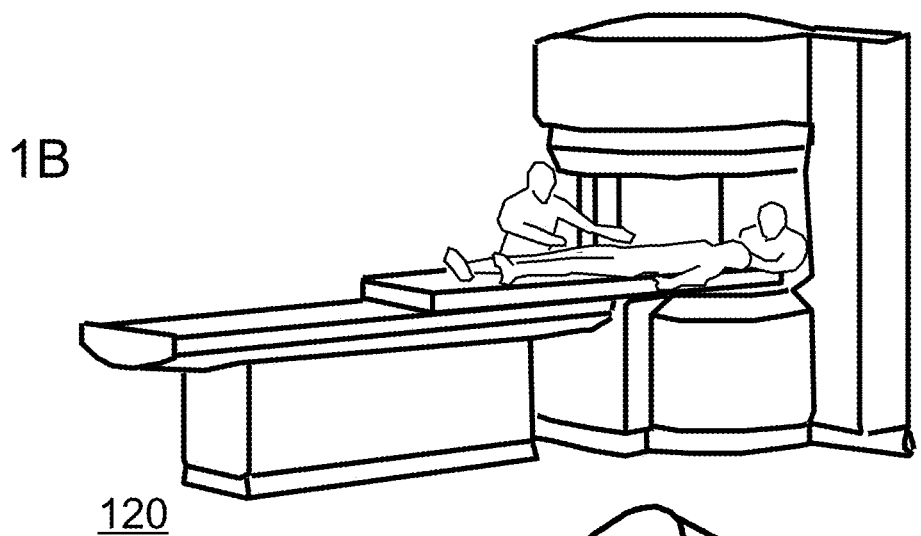
Figure 1:
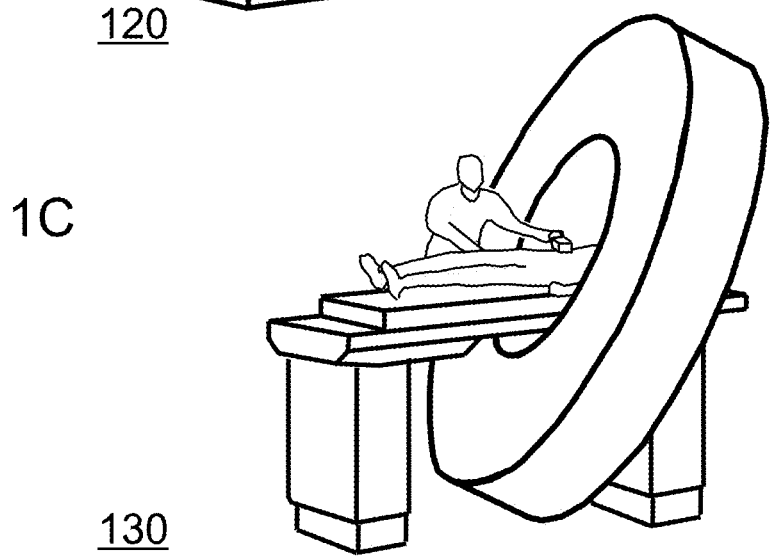

FIG. 1A to FIG. 1C are external views of the MRI apparatus. FIG. 1A illustrates the MRI apparatus 100 of a horizontal magnetic field type 100 that uses a tunnel-type magnet for generating a static magnetic field by a solenoid coil. FIG. 1B illustrates the MRI apparatus 120 of a hamburger-type (open-type) vertical magnetic field system in which the magnets are separated vertically so as to enhance the sense of openness. FIG. 1C illustrates the MRI apparatus 130 using the same tunnel-type magnet as FIG. 1A, the magnet having a reduced depth and put in a slanting position, thereby enhancing the sense of openness.

In the present embodiments, the MRI apparatus having any of those external views can be employed. However, those are just examples and forms of the MRI apparatus according to the present embodiments are not limited to those examples. In the present embodiments, any of publicly known various MRI apparatuses can be employed, whatever the form or type of the apparatus is. The MRI apparatus 100 will be used as a representative example in the following, if there is no need of particular differentiation.

[Configuration of MRI Apparatus]

Figure 2:
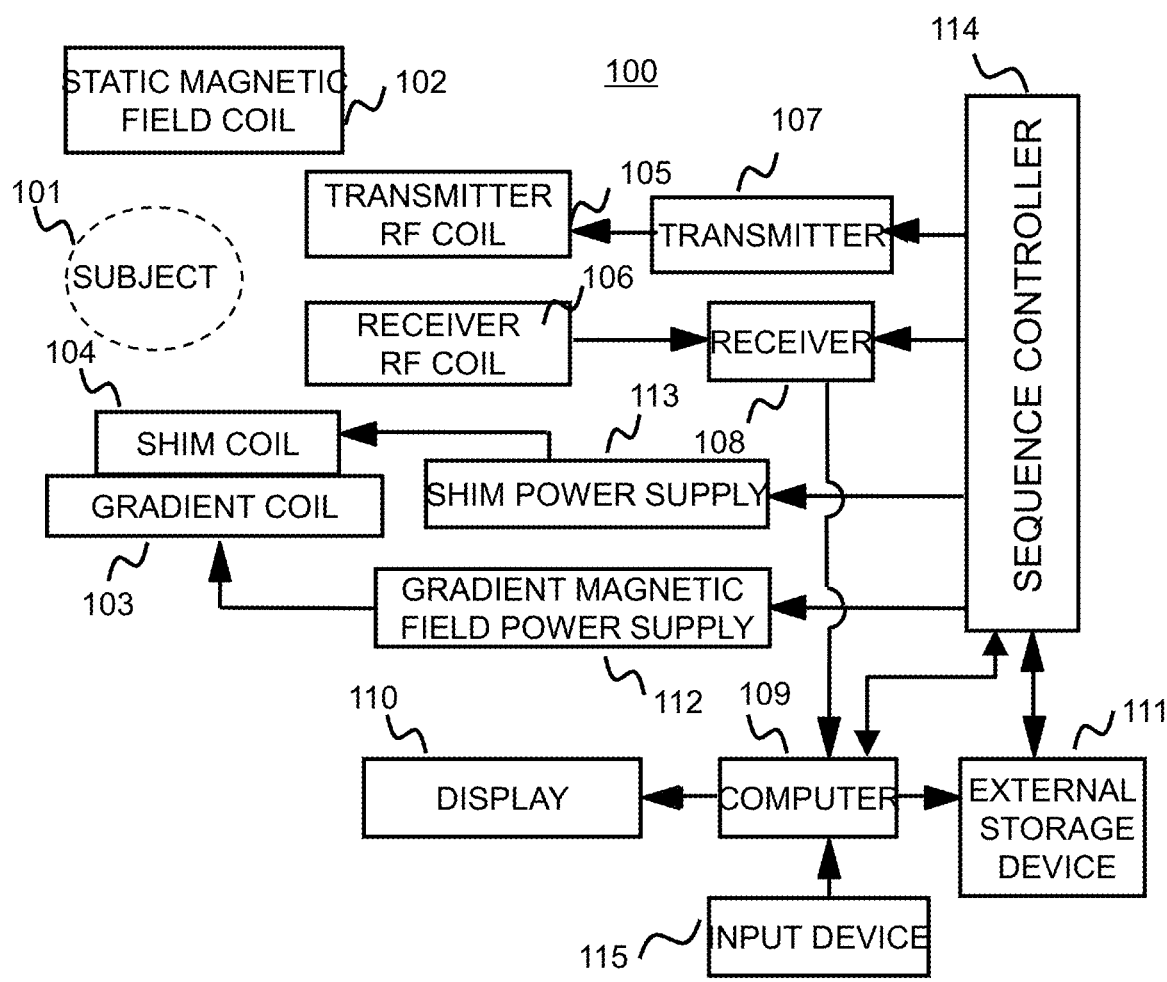
FIG. 2 is a block diagram showing a schematic configuration of the MRI apparatus according to an embodiment of the present invention.

FIG. 2 is a functional block diagram of the MRI apparatus 100 according to the present embodiment. As illustrated, the MRI apparatus 100 of the present embodiment comprises a static magnetic field generator provided with a static magnetic field coil 102 for generating a static magnetic field in the space where the subject 101 is paced, a shim coil 104 for adjusting a static magnetic field distribution, a transmitter RF coil 105 (hereinafter, simply referred to as "transmitter coil") for transmitting an RF magnetic field to a measurement area of the subject 101, a receiver RF coil 106 (hereinafter, simply referred to as "receiver coil") for receiving a nuclear magnetic resonance signal generated from the subject 101, a gradient coil 103 for applying a gradient magnetic field to each of the directions; x-direction, y-direction, and z-direction, so as to add positional information to the nuclear magnetic resonance signal generated from the subject 101, a transmitter 107, a receiver 108, a computer 109, a gradient magnetic field power supply 112, a shim power supply 113, and a sequence controller 114. Among those constitutional elements above, the elements excluding the computer 109 (and the sequence controller 114) may collectively be referred as a measuring unit.

The static magnetic field generator comprises a non-superconductive or superconductive static magnetic field coil 102, a static magnetic field generating magnet, and so on. In response to the structures of the MRI apparatuses 100, 120, and 130, respectively shown in FIG. 1A, FIG. 1B, FIG. 1C, various forms of static magnetic field generator may be employed.

The transmitter coil 105 and the transmitter 107 function as a transmission unit, and RF signals generated by the transmitter 107 are transmitted to the transmitter coil 105, thereby allowing the transmitter coil to emit an RF magnetic field. The receiver coil 106 and the receiver 108 function as the receiver, and the nuclear magnetic resonance signal detected by the receiver coil 106 is transferred to the computer 109 via the receiver 108. In FIG. 2, there is described the case where the transmitter coil 105 and the receiver coil 106 separately provided are used. However, it is possible to configure such that one coil is employed, serving both the transmitter coil 105 and the receiver coil 106 functions.

The gradient coil 103 and the shim coil 104 are driven by the gradient magnetic field power supply 112 and the shim power supply 113, respectively. The gradient coil 103 and the gradient magnetic field power supply 112 function as a gradient magnetic field generator.

The sequence controller 114 controls the operation of the gradient magnetic field power supply 112 being a power source for driving the gradient coil 103, the shim power supply 113 being a power source for driving the shim coil 104, the transmitter 107, and the receiver 108, thereby controlling application of the gradient magnetic field and the RF magnetic field, and receiving timing of the nuclear magnetic resonance signal. A time chart of the control is referred to as a pulse sequence, whose settings are previously configured depending on the measurement, and it is stored, for example, in a storage device being provided in the computer 109 as described below.

In the MRI apparatus of the present embodiment, there is stored a pulse sequence for generating a nuclear magnetic resonance signal including an influence from a predetermined physical property of the subject. This predetermined physical property is a value reflecting oxygen content characteristics of the subject. This value may be, for example, magnetic susceptibility, $R_2^*$, and "difference R' between $R_2^*$ and $R_2$". Here, $R_2$ and $R_2^*$ represent respectively, a reciprocal of real transverse relaxation time $T_2$, and a reciprocal of apparent transverse relaxation time $T_2^*$, and they can be calculated by using a plurality of echo signals at different TEs. Generally, $R_2^*(T_{2*})$ is calculated by using a gradient echo, and $R_2(T_2)$ is calculated by using a spin echo.

The computer 109 controls the entire operation of the MRI apparatus 100, along with performing various computations on the nuclear magnetic resonance signals being received. In the present embodiment, the computer generates a complex image at any echo time, a distribution of the physical property, a distribution of an oxygen extraction fraction, and the like. The computer 109 is an information processor including a CPU, a memory, and a storage device, and the computer 109 is connected to other devices, such as a display 110, an external storage device 111, and an input device 115.

The display 110 is an interface configured to display information for an operator, such as a result obtained by computations. The input device 115 is an interface configured to allow the operator to input conditions, parameters, and the like, necessary for the measurement and computations performed in the present embodiment. The user is allowed to input measurement parameters, such as the number of echoes to be measured, an echo time, and an echo interval, via the input device 115. The external storage device 111, along with the storage device within the computer 109, holds data such as the data used in various computations executed by the computer 109, data obtained through the computations, conditions and parameters being inputted.

FIGS. 3A and 3B illustrate configuration examples of the implement the computer 109 where the functions described above are implemented. As shown in FIG. 3A, the computer 109 of the present embodiment includes, a measurement controller 310 configured to measure complex signals of nuclear magnetic resonance signals (echo signals), generated from the subject in response to irradiation of RF magnetic field pulses, an image reconstructor 320 configured to reconstruct a complex image where a pixel value is a complex value, from the complex signals measured by the measurement controller 310, and an oxygen extraction fraction distribution calculator 330 configured to calculate a distribution of the oxygen extraction fraction from the complex image reconstructed by the image reconstructor 320. Details of the oxygen extraction fraction distribution calculator 330 will be described later.

A CPU loads programs (software) held in the storage device into a memory and executes those programs, whereby those functions of the elements in the aforementioned computer 109 are implemented. The storage device or the external storage device 111 may store various data used for processing of the functions, and various data generated in process. Another information processor that is independent of the MRI apparatus 100, data transmittable and receivable thereto and therefrom, may implement at least one of the various functions implemented by the computer 109. Furthermore, all or a part of the functions may be implemented by hardware such as ASIC (Application Specific Integrated Circuit) and FPGA (Field-Programmable Gate Array).

Figure 4:
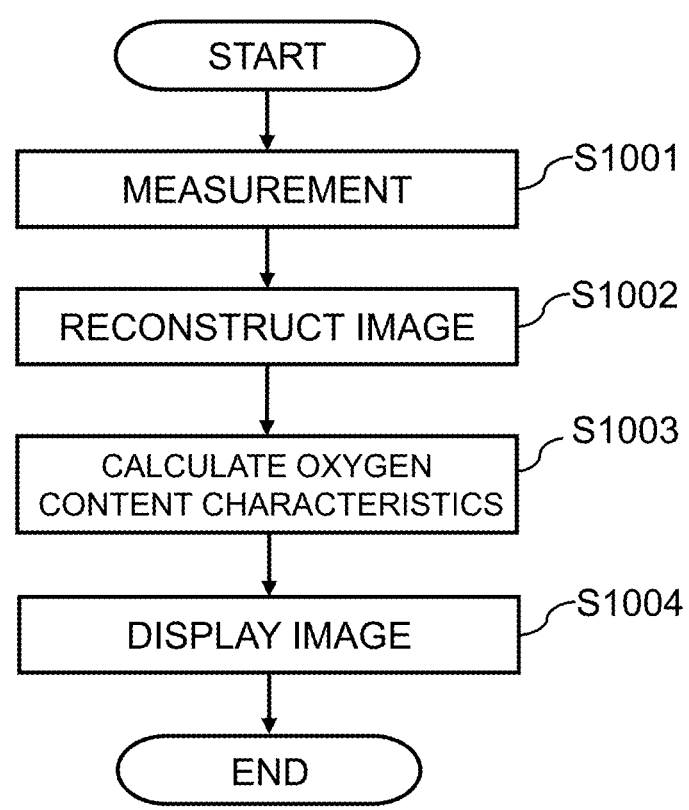
FIG. 4 is a flowchart showing a processing performed by the computer as shown in FIGS. 3A and 3B.

Next, an overview of the operation of the MRI apparatus (mainly, the computer 109) of the present embodiment will be described. FIG. 4 is a flowchart showing the operation. In this example, there will be illustrated the case where an oxygen extraction fraction is calculated as the oxygen content characteristics. Firstly, the measurement controller 310 controls the sequence controller 114 according to a predetermined pulse sequence, thereby measuring an echo signal at a preset echo time (step S1001). Then, the image reconstructor 320 places thus obtained echo signals in k-space, applies Fourier transform thereto, thereby reconstructing a complex image I (step S1002). The oxygen extraction fraction distribution calculator 330 calculates from the complex image, a distribution of the physical property reflecting the oxygen extraction fraction, and performs an oxygen extraction fraction distribution calculation process for calculating the distribution of the oxygen extraction fraction from the physical property distribution (step S1003).

In the step S1003 for calculating the distribution of the oxygen extraction fraction, the physical property image (also referred to as "physical property distribution") is separated into a plurality of tissue images (tissue separation process). Specifically, the complex image as a base of the physical property image, targets a desired area in the subject, for example, the head (brain), and the physical property image also represents the physical property of this area. The area in the subject may include a plurality of different tissues, for example, in the case of the brain, brain parenchyma and blood vessels. In this processing, the physical property image is separated into tissue-specific physical property images for different tissues, by using pixel values. The physical property images obtained after the separation are referred to as separated tissue images. This tissue separation process includes the case where a desired one tissue image is isolated from the remaining tissues, and a plurality of separated tissue images are not necessarily obtained. Thereafter, a process for converting the pixel value as to one of the separated tissue images is performed, from the physical property to the oxygen content characteristics (conversion process). Accordingly, the oxygen content characteristics can be obtained as to the tissue being separated. By using the separated tissue image after the conversion process (that is, the value of oxygen content characteristics), the oxygen content characteristics of the target subject area are estimated, thereby obtaining a distribution of the oxygen content characteristics. If necessary, a correction, for example, partial volume effect correction, may be performed in order to enhance the accuracy.

Thereafter, thus calculated distribution of the oxygen extraction fraction is displayed on the display 110 (step S1004). When the distribution of the oxygen extraction fraction is displayed on the display 110, there may also be displayed other images in addition to the oxygen extraction fraction distribution calculated in step S1003, if necessary, which are obtained in the course of calculating the oxygen extraction fraction distribution.

Figure 3:
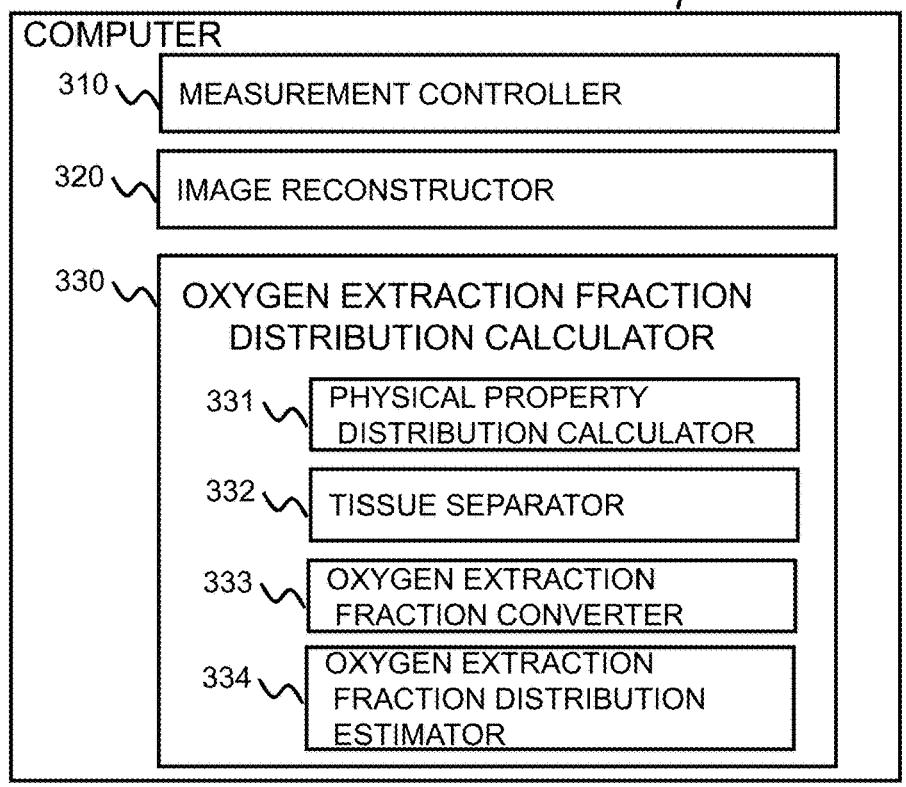
FIGS. 3A and 3B are functional block diagrams of a computer commonly used in the embodiments.
Figure 3:
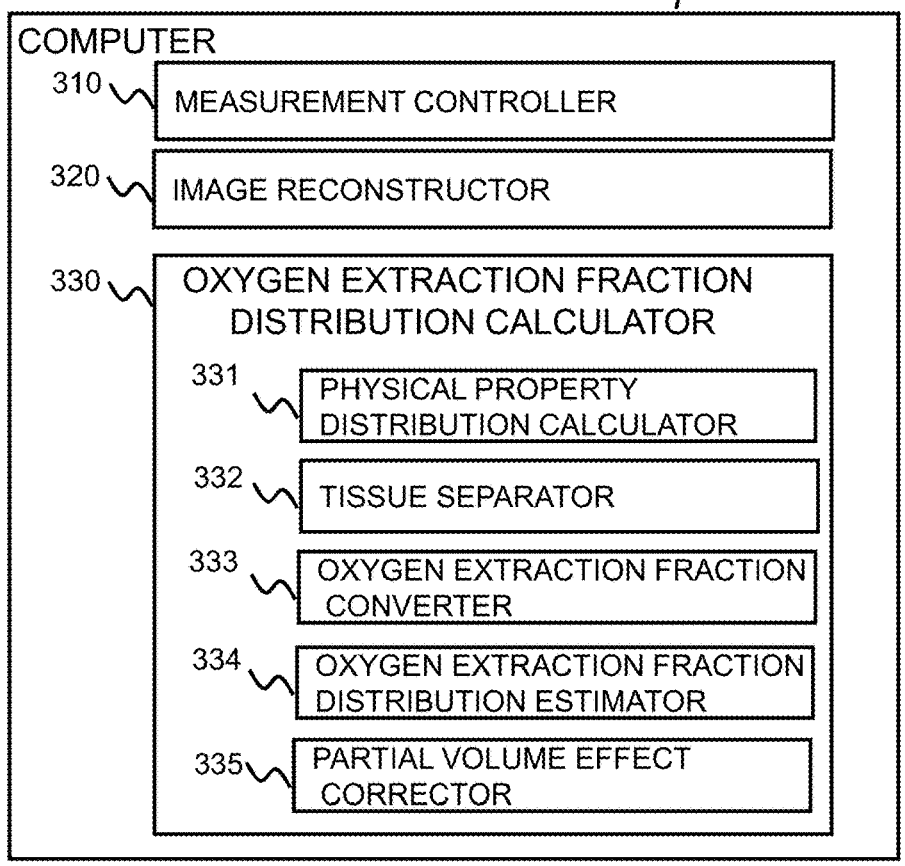

Each unit of the oxygen extraction fraction distribution calculator 330 as shown in FIG. 3 allows implementation of the processing as described above. As shown in FIG. 3A, the oxygen extraction fraction distribution calculator 330 comprises a physical property distribution calculator 331 configured to calculate from the complex image I, the physical property distribution reflecting the oxygen extraction fraction, a tissue separator 332 configured to calculate from thus calculated physical property distribution, separated tissue images of at least two separated living tissues, an oxygen extraction fraction converter 333 configured to convert any of the separated tissue images into a pixel value corresponding to the oxygen extraction fraction, and an extraction fraction distribution estimator 334 configured to estimate the distribution of the oxygen extraction fraction based on the condition that a value of any pixel is substantially equal to a mean value of surrounding pixels. As shown in FIG. 3B, the oxygen extraction fraction distribution calculator 330 may also comprise a corrector for correcting the estimated distribution of the oxygen extraction fraction that is calculated by the oxygen extraction fraction distribution estimator 334. In the illustrated example, the oxygen extraction fraction distribution calculator 330 comprises a partial volume effect corrector 335 configured to correct the oxygen extraction fraction that is lowered due to a partial volume, based on the condition that the oxygen extraction fraction in any vein is substantially equal to the mean value of oxygen extraction fraction in the whole brain, and after the correction, a final distribution of the oxygen extraction fraction is obtained.

There will now be described in detail a process performed by the computer 109, according to specific embodiments. In the following embodiments, descriptions will be provided assuming that a target portion (area) is the brain, and as the oxygen content characteristics distribution, the oxygen extraction fraction distribution in the brain (parenchyma) is obtained. The configuration of the computer 109 in the following embodiments is the same as shown in FIG. 3, but the "physical property distribution calculator 331" in FIG. 3 shall be read as "susceptibility distribution calculator" in the following embodiments.

First Embodiment

In the present embodiment, a susceptibility distribution is calculated as the physical property, and the oxygen extraction fraction distribution is calculated from the susceptibility distribution. In the tissue separation process, the image of veins is separated from other tissues, and a venous distribution is calculated. With reference to a processing flowchart as shown in FIG. 4, there will now be described a processing of the present embodiment.

[Measurement: S1001]

The measurement controller 310 operates the sequence controller 114, according to a pulse sequence that is configured based on parameters inputted by a user via the input device 115, and performs measurement for acquiring a nuclear magnetic resonance signal (echo signal) at a predetermined echo time (TE). The sequence controller 114 controls the measuring unit and performs measurement, in response to an instruction from the measurement controller 310. In the present embodiment, an echo signal at any selected one echo time is obtained.

An example of the pulse sequence will be described, being used in the measurement by the measurement controller 310. In the present embodiment, for example, GrE (Gradient Echo) type pulse sequence may be employed. An image obtained by this GrE type pulse sequence sharply reflects the oxygen extraction fraction in the living tissue.

Figure 5:
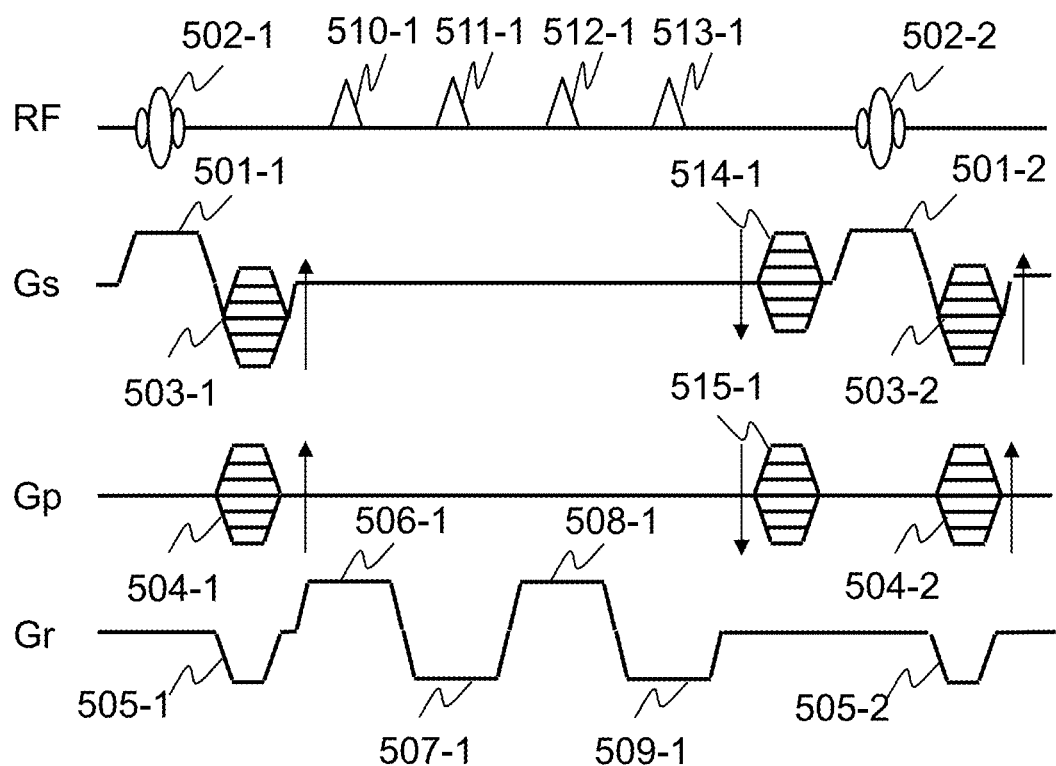
FIG. 5 illustrates one example of a pulse sequence used for acquiring data for a complex image.

FIG. 5 illustrates an RSSG (RF-spoiled-Steady-state Acquisition with Rewound Gradient-Echo)-Multiecho sequence 550, as an example of the GrE-system pulse sequence. In this figure, RF, Gs, Gp, and Gr represent, respectively, an RF magnetic field, a slice gradient magnetic field, a phase encoding gradient magnetic field, and a readout gradient magnetic field.

In the RSSG sequence 550, a radio-frequency (RF) magnetic field pulse 502 is applied along with application of a slice gradient magnetic field pulse 501, thereby exciting magnetization of a predetermined slice within the subject 101. Then, a slice encoding gradient magnetic field pulse 503 and a phase encoding gradient magnetic field pulse 504 are applied, so as to add positional information in the slice-direction and in the phase-encoding direction, to a phase of the magnetization.

After applying a readout gradient magnetic field pulse 505 for dephasing, which disperses the phase of nuclear magnetization within a pixel, nuclear magnetic resonance signals (echoes) 510, 511, 512, and 513 are measured, along with applying readout gradient magnetic field pulses 506, 507, 508, and 509 for adding positional information in the readout direction. And finally, a slice encoding gradient magnetic field pulse 514 and a phase encoding gradient magnetic field pulse 515 for rephasing are applied, for convergence of the phase of nuclear magnetization that has been dephased by the slice encoding gradient magnetic field pulse 503 and the phase encoding gradient magnetic field pulse 504.

The measurement controller 310 executes the procedures above, repeatedly every repetition time TR, while varying strength of the slice encoding gradient magnetic field pulses 503 and 514 (slice-encoding count ks) and of the phase encoding gradient magnetic field pulses 504 and 515 (phase-encoding count kp), and the phase of the RF pulse 502, whereby echoes necessary for acquiring one image are measured as to each echo time. In this situation, the phase of the RF pulse 502 may be incremented by 117 degrees, for instance, in order to eliminate the influence of transverse magnetization remaining after the previous excitation. In FIG. 5, the numbers following the hyphen indicate the number of repetitions.

At each measured echo, Flow Compensation gradient pulse may be applied to each axis for compensating for an impact of flow, such as bloodstream.

The measured echoes are arranged in three-dimensional k-space (memory space) having kr, kp, and ks as coordinate axes. In this situation, one echo occupies one line that is parallel to the kr axis in k-space. A magnitude image obtained by this RSSG sequence 550 may become a T1 (longitudinal relaxation time) weighted image for the echo with a short TE, whereas it may become a T2* weighted image reflecting the phase dispersion in the pixel for the echo with a long TE.

The RSSG sequence 550 illustrated in FIG. 5 is one method of Cartesian imaging for acquiring data in parallel to the coordinate axes in k-space. However, any sequence may be employed to acquire data in any k-space domain. For example, non-Cartesian imaging may be employed, such as radial scanning for acquiring data in k-space in rotational manner. In the example here, images are obtained at every echo of multi-echoes from 510 to 513 at different TEs, but a k-space scanning method (multi-echo planar imaging method) of echo-planar type that gives different encoding to each echo may also be applicable. It is further possible to measure one complex image, by using a sequence for measuring an echo at one TE, instead of obtaining complex images at a plurality of echo times.

[Image Reconstruction: S1002]

Next, the image reconstructor 320 applies Fourier transform to the echo signal at the echo time TE, placed in k-space in step S1001, and calculates a complex image I.

[Oxygen Extraction Fraction Distribution Calculation Process (Oxygen Content Characteristic Calculation): S1003]

The oxygen extraction fraction distribution calculator 330 calculates a distribution of the oxygen extraction fraction from the complex image I that is reconstructed by the image reconstructor 320. The oxygen extraction fraction distribution represents an image of oxygen content consumed by the living tissues.

Figure 6:
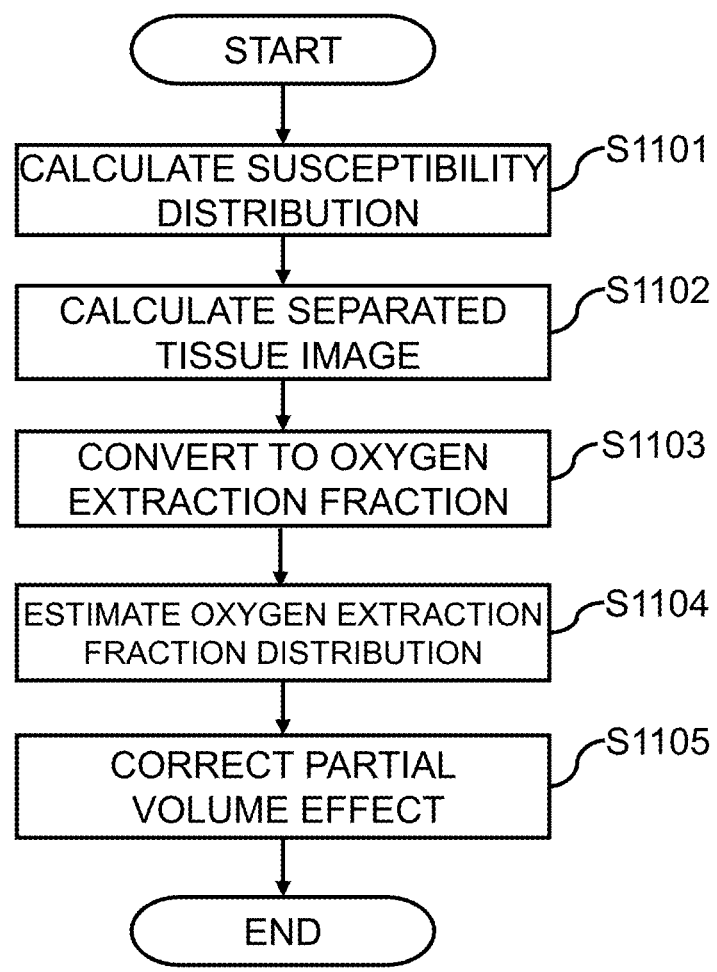
FIG. 6 is a flowchart of a process for calculating a distribution of an oxygen extraction fraction according to a first embodiment.

With reference to FIG. 6, processing of the oxygen extraction fraction distribution calculator 330 (S1003) in the present embodiment will be described in detail. In the processing of S1003 as shown in FIG. 6, the physical property distribution calculator 331 firstly calculates a susceptibility distribution from the complex image I (S1101). The tissue separator 332 separates thus calculated susceptibility distribution in association with at least two types of living tissues, and calculates separated tissue images (tissue-specific susceptibility distributions) (S1102). Then, the oxygen extraction fraction converter 333 converts the pixel value (magnetic susceptibility) as to any of the separated tissue images, into a pixel value corresponding to the oxygen extraction fraction (S1103). Thereafter, the distribution of the oxygen extraction fraction in the whole target area is estimated, on the basis of a condition that a value of any pixel is substantially equal to a mean value of the surrounding pixels in the separated tissue image (S1104). If necessary, a correction for enhancing accuracy of the oxygen extraction fraction distribution is performed, and then a final distribution of the oxygen extraction fraction is obtained (S1105). For example, processing for correcting a partial volume effect is performed. This correction process is to correct an error based on a difference between the pixel size of the image being a processing target and the size of the tissue contributing to the magnetic susceptibility as to each of the pixels used for estimating the oxygen extraction fraction. The correction is performed on the estimated oxygen extraction fraction distribution thus obtained, to correct the oxygen extraction fraction that is lowered due to a partial volume, based on the condition that the oxygen extraction fraction in any vein is substantially equal to a mean value of the entire oxygen extraction fraction in the whole brain.

Hereinafter, there will be described in detail, the processing performed by each unit of the oxygen extraction fraction distribution calculator 330 of the present embodiment.

[Calculate Susceptibility Distribution: S1101]

The susceptibility distribution calculator 331 calculates a susceptibility distribution, by using the QSM (quantitative susceptibility mapping) method, from phase information (phase image) of the measured complex image I. A method for calculating the susceptibility distribution by using the QSM method is publicly known, and an outline thereof will be described.

In the QSM method, local magnetic field variations caused by a magnetic susceptibility difference between living tissues are calculated from the phase image taken by the Gradient Echo (GrE) method. A relative magnetic field variation (magnetic field distribution) $\delta(r)$ that is caused by the magnetic susceptibility difference between tissues is expressed by the following formula 1, assuming a position vector as r:

[Formula 1]

$$\delta(r) = -\frac{\phi(r)}{\gamma \cdot B_0 \cdot TE} \quad (1)$$

where $\varphi(r)$ is a phase image, $\gamma$ is a nuclear gyromagnetic ratio of proton, $B_0$ is static magnetic field strength, and TE is echo time.

The magnetic field distribution $\delta(r)$ is expressed by the following formula 2, using the susceptibility distribution $\chi(r)$ within a living body, according to the Maxwell's equations with regard to a static magnetic field:

[Formula 2]

$$\delta(r) = \frac{1}{4\pi} \int \chi(r') \frac{3\cos^2\alpha - 1}{|r' - r|} dr'^3 \quad (2)$$
$$= d(r) \otimes \chi(r)$$

where $\alpha$ is an angle made by the vector (r'-r) and the static magnetic field direction, and d(r) is a point-dipole magnetic field.

As indicated by the formula 2, the magnetic field distribution $\delta(r)$ is represented by a convolution integral of the susceptibility distribution χ(r) and the point-dipole magnetic field d(r). Therefore, both sides of the formula 2 are subjected to the Fourier transform, whereby the formula 2 is transformed to the following formula 3:

[Formula 3]

$$\Delta(k) = \left(\frac{1}{3} - \frac{k_z^2}{k_x^2 + k_y^2 + k_z^2}\right) \cdot X(k) \quad (3)$$
$$= D(k) \cdot X(k)$$

where k=($k_x$, $k_y$, $k_z$) indicates the position vectors in k-space, Δ(k), X(k), and D(k) are Fourier components, respectively of the magnetic field distribution δ(r), the susceptibility distribution χ(r), and the point-dipole magnetic field d(r).

As indicated by the formula 3, the Fourier component X(k) of the susceptibility distribution can be obtained by dividing the Fourier component Δ(k) of the magnetic field distribution by the Fourier component D(k) of the point-dipole magnetic field. However, according to the formula 3, the reciprocal of D(k) diverges near the region D(k)=0, and thus X(k) cannot be calculated directly.

This region where D(k)=0 is referred to as a magic angle, and this forms a reverse bi-cone region that has an apex angle approximately twice as large as 54.7° with respect to the magnetic field direction. Due to this magic angle, the QSM method that estimates the susceptibility distribution based on the magnetic field distribution results in an ill-conditioned inverse problem, and thus several solutions are suggested.

Representative methods for those solutions include, a method of iterating a smoothing process on the susceptibility distribution calculated from the magnetic field distribution, under the constraints based on the relational expression between the magnetic field and the magnetic susceptibility (the method described in the Japanese Patent Application No. 2014-228843 by the inventors of the present application), the TKD (Truncated-based K-space Division) method for calculating the susceptibility distribution according to computations in k-space of the magnetic field distribution and the point-dipole magnetic field, the Iterative SWIM (Susceptibility Weighted Imaging and Mapping) method that combines through iterative operations, the susceptibility distribution calculated by the TKD method, with the susceptibility distribution obtained by extracting a fine structure by threshold processing, and the MEDI (Morphology enabled dipole inversion) method that uses a regularized least squares method.

The susceptibility distribution calculator 331 of the present embodiment uses those methods above to calculate a quantitative susceptibility distribution (QSM). In the present embodiment, any methods are applicable in the present embodiment for calculating the quantitative susceptibility distribution.

[Calculate Separated Tissue Image: S1102]

The tissue separator 332 calculates the separated tissue images, obtained by separating the calculated susceptibility distribution, in association with at least two types of living tissue. In the present embodiment, a region of veins is extracted from the susceptibility distribution calculated by the physical property distribution calculator 331, and the susceptibility distribution in veins, and the susceptibility distribution in the remaining tissues are calculated respectively.

Figure 7:
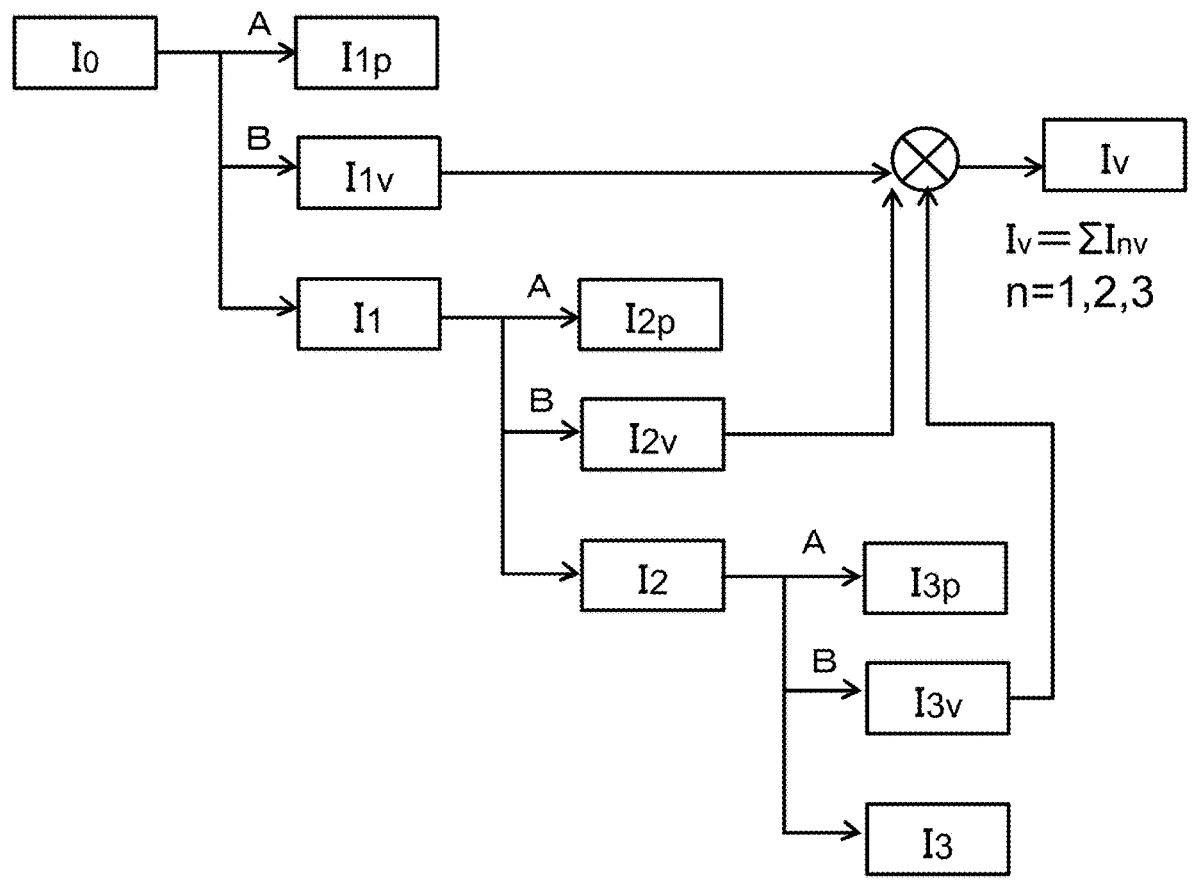
FIG. 7 illustrates a tissue separation process according to the first embodiment.
Figure 7:
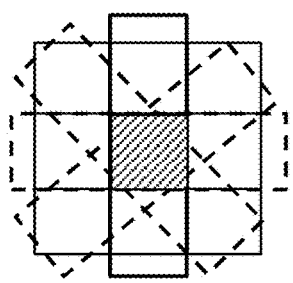
Figure 7:
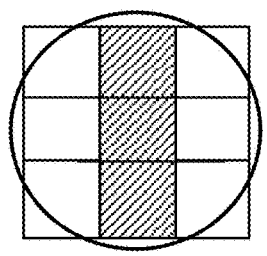

There may be several methods to separate the susceptibility distribution into the tissue-specific susceptibility distributions. In the example here, there will be described a method to calculate the susceptibility distribution in veins, by using morphology filter bank. The morphology filter bank is a process that is based on morphological operations for extracting a feature from a given image according an opening process and a top-hat transformation (see the IEICE Technical Report MI2010-101 (2011-1) for the details), and this process is repeated along with varying the size of a structuring element used for the morphological operations. Specifically, as shown in FIG. 7, the calculated susceptibility distribution is subjected to the top-hat transformation using multiple linear structuring elements obtained by changing the angle of the linear structuring element three-dimensionally, and a particulate component is separated. Then, according to the top-hat transformation using a spherical structuring element, a venous component is separated. With the configuration above, an original image $I_0$ is separated into the particulate component image $I_{1P}$, a vascular component image $I_{1v}$, and a smoothed image $I_1$. The smoothed image $I_1$ being separated is subjected to the top-hat transformation again, using a plurality of structuring elements increased in size, and it is separated into the particulate component image $I_{2P}$, the vascular component image $I_{2v}$, and the smoothed image $I_2$. This processing is repeated with increasing the size of the structuring element. Thereafter, by taking the sum of the vascular component images separated in each steps, it is possible to extract a blood vessel with a diameter equal to or less than the diameter associated with the maximum value of the size of the structuring element. In FIG. 7, there is shown the case where the repeat count is three, but the repeat count may be set to any number.

In the present embodiment, since the venous component is separated after separating the particulate component, it is possible to calculate the susceptibility distribution in veins, excluding tissues to which iron protein (Ferritin) is deposited, such as pallidum, red nucleus, and substantia nigra, which may cause high susceptibility in the susceptibility distribution.

There has been described the separation process where the morphology filter bank is used for the separation of the susceptibility distribution in veins from the susceptibility distribution in the remaining tissues, but the separation process is not limited to the method above. For example, a small area made up of a plurality of pixels may be set in the susceptibility distribution (image), a mean value and a standard deviation of the magnetic susceptibility within this small area are calculated, and pixel values that falls outside the range (mean value+N×standard deviation) may be extracted as veins (N is any real number). In addition, various filters such as a differentiation filter may be combined. It is further possible that the absolute value (magnitude) of the image acquired in S1002 of FIG. 4 is used to separate the venous tissue, generating a mask where the venous area is set to 1 and the remaining area is set to 0, and then, the susceptibility distribution is multiplied by the mask. It should be noted, however, depiction performance to depict a capillary or a similar thing is higher in the susceptibility distribution, than the magnitude image, and thus a method that uses the susceptibility distribution should be more preferable.

[Conversion to Oxygen Extraction Fraction: S1103]

The oxygen extraction fraction converter 333 converts any of the separated tissue images of at least two living tissues to the oxygen extraction fraction. In the present embodiment, the susceptibility distribution in veins is converted into the oxygen extraction fraction. It is known that the magnetic susceptibility in veins is proportional to the concentration of deoxyhemoglobin, that is, it is proportional to the oxygen extraction fraction. Specifically, the oxygen extraction fraction can be calculated according to formula 4 (Jan Sedlacik et al; "Validation of Quantitative Estimation of Tissue Oxygen Extraction Fraction and Deoxygenated Blood Volume Fraction in Phantom and In Vivo Experiments by Using MRI", Magnetic Resonance in Medicine, 2010, vol. 63, Equation 6, pp. 910-921).

[Formula 4]

$$OEF = \frac{\chi_v}{4\pi\Delta\chi_{do} \cdot Hct} \quad (4)$$

where a susceptibility difference between the vein and the other living tissue is $\chi_v$, hematocrit (numeric value indicating the volume percentage of blood cells in blood) is Hct, and an arteriovenous difference of susceptibility per hematocrit is $\Delta\chi_{do}$.

It is said that the hematocrit value is approximately 0.42 in normal men, and 0.38 in normal women. It is known that the arteriovenous difference of susceptibility $\Delta\chi_{do}$ per hematocrit is 0.18 ppm (CGS unit system). Therefore, if a calculated susceptibility difference $\Delta\chi_v$ between the vein and the other living tissue is obtained, it is possible to convert the obtained value to the venous OEF. It should be noted that a blood test may be performed for the same subject separately from the MRI examination, and a result of the blood test may be substituted into the hematocrit value.

[Estimate Oxygen Extraction Fraction Distribution: S1104]

The oxygen extraction fraction distribution estimator 334 estimates a distribution of the oxygen extraction fraction in whole tissues corresponding to a target subject, for example, brain parenchyma, based on a constraint condition (first condition) that, in the susceptibility distribution in veins having been converted to the oxygen extraction fraction, a value of any pixel is substantially equal to a mean value of surrounding pixels. Following formula 5 is established, where a mask (binary mask) is M, setting a target area to 1, and the remaining area (e.g., an area such as a brain surface) to 0, a radius of a local area estimated as satisfying the first condition is r, a spherical kernel with the radius r is ρ, and delta function is δ, assuming that the oxygen extraction fraction $OEF_t$ of the living tissue (target area) does not change significantly within the range where the radius is r.

[Formula 5]

$$M(\rho-\delta) \otimes OEF_t = 0 \quad (5)$$

where ⊗ represents convolution integration

The binary mask M can be created in advance from the magnitude image, and the mask may be identical to the mask used in calculating the susceptibility distribution, or may have a smaller range.

Formula 5 can be rewritten to formula 6, using the Fourier transform operator F and the inverse Fourier transform operator $F^{-1}$.

[Formula 6]

$$MF^{-1}(C-\Delta)F \cdot OEF_t = 0 \quad (6)$$

In formula 6, C represents the Fourier component of kernel ρ (C=Fρ) and Δ represents the Fourier component of the delta function δ (Δ=Fδ). It is only aimed to obtain the tissue oxygen extraction fraction $OEF_t$ that satisfies the formula 6. Therefore, in the present embodiment, the oxygen extraction fraction $OEF_t$ satisfying the formula 6 is calculated, under an additional constraint condition (second condition) that a local mean value of the venous oxygen extraction fraction $OEF_v$ is equal to a local mean value of the tissue oxygen extraction fraction $OEF_t$. That is, the value of "$OEF_t$" that minimizes the formula 7 is obtained.

[Formula 7]

$$\underset{OEF_t}{\operatorname{argmin}} \|MF^{-1}(C-\Delta)F \cdot OEF_t\|_2^2 + \lambda \|MF^{-1}CF(OEF_v - OEF_t)\|_2^2 \quad (7)$$

where the first term represents the first condition, and the second term represents the second condition. In addition, λ represents a regularization parameter, being a parameter for controlling a degree of influence of the constraint conditions. The value of λ typically falls into the range from 0.1 to 10.0. According to the processing above, by using the venous oxygen extraction fraction $OEF_v$, the tissue oxygen extraction fraction $OEF_t$ can be estimated.

In the present embodiment, the tissue oxygen extraction fraction $OEF_t$ is estimated according to the minimization process of formula 7, but the present embodiment is not limited to this method. For example, it is possible to employ a smoothing process by the local mean value of the venous oxygen extraction fraction $OEF_v$ or by Gaussian filtering of the venous oxygen extraction fraction $OEF_v$.

[Partial Volume Effect Correction: S1105]

The partial volume effect corrector 335 performs a partial volume effect correction on the tissue oxygen extraction fraction $OEF_t$ calculated in S1104. The venous oxygen extraction fraction $OEF_v$ used for calculating the tissue oxygen extraction fraction $OEF_t$ in S1103 is calculated to be a small value for the vein that is smaller than a pixel size, due to the partial volume effect caused by the remaining living tissue included in the pixel (partial volume effect). Therefore, it is necessary to correct a reduction in the oxygen extraction fraction due to the partial volume effect. The partial volume effect corrector 335 firstly calculates a correction factor (partial volume effect correction factor) for correcting the oxygen extraction fraction that has been reduced due to the partial volume effect, based on the condition that the oxygen extraction fraction in any selected vein is equal to a mean value of the oxygen extraction fraction in the whole brain. Preferably, this selected vein should be regarded as enabling to represent the oxygen extraction fraction in the whole brain, and it may be a thick vein, for example, venous sinus.

Following formula 8 represents the condition as described above (the condition where the oxygen extraction fraction in any selected vein is equal to the mean value of the oxygen extraction fraction in the whole brain, where the oxygen extraction fraction in the selected vein is $OEF_{SSS}$, the number of pixels within the binary mask M is N, and the tissue oxygen extraction fraction at the pixel position i is $OEF_t(i)$. PVC is the partial volume effect correction factor for satisfying the formula 8.

[Formula 8]

$$OEF_{SSS} = PVC \cdot \frac{\sum_{i=1}^{N} OEF_i(i)}{N} \quad (8)$$

The oxygen extraction fraction in the selected vein $OEF_{SSS}$ may be obtained, for example, by choosing one or more pixels corresponding to this selected vein, from the image (susceptibility distribution image) that is separated as a venous image in the tissue separation process, and subjecting the pixels to the conversion process in S1103.

Then, the partial volume effect corrector 335 uses the partial volume effect correction factor PVC satisfying the formula 8 to correct the oxygen extraction fraction in each pixel according to formula 9. Then, a final distribution of the oxygen extraction fraction $OEF(i)_{corrected}$ can be calculated.

[Formula 9]

$$OEF(i)\text{corrected}=PVC \cdot OEF_i(i) \quad (9)$$

According to the processing from steps S1101 to S1105, the oxygen extraction fraction distribution calculation process S1003 as shown in FIG. 4 is completed. The flowchart shown in FIG. 6 indicates just an example of the processing, and a part of the processing may be excluded, or the order of steps may be changed in the present embodiment. For example, the partial volume effect correction in FIG. 6 may be skipped, or the partial volume effect correction may be performed after calculating the separated tissue image or after the conversion to the oxygen extraction fraction. A smoothing method by a filter as appropriate may be performed, other than the partial volume effect correction. Furthermore, by using thus calculated oxygen extraction fraction, other oxygen content characteristics such as oxygen saturation and metabolic rate of oxygen may also be calculated, for instance.

Figure 8:
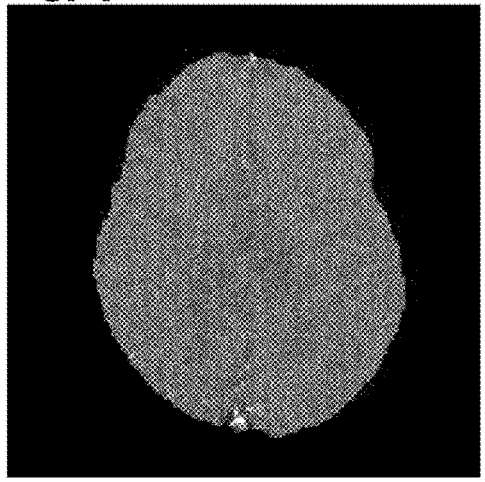
FIGS. 8A, 8B, and 8C illustrate distributions calculated in the respective processes according to the first embodiment.
Figure 8:
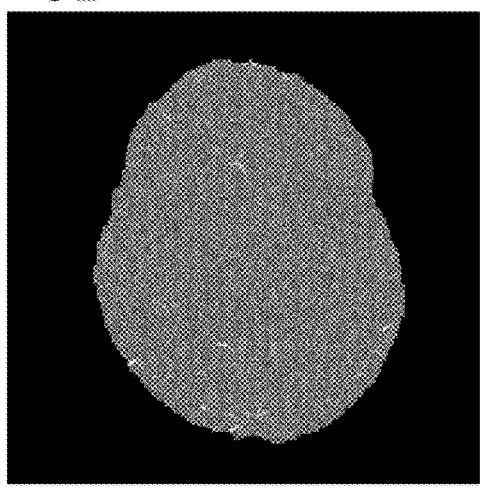
Figure 8:
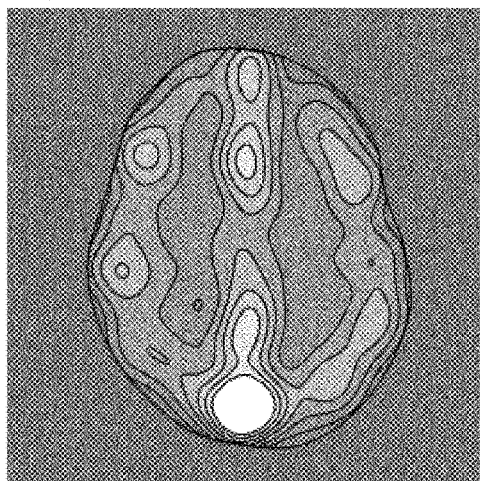

FIG. 8 illustrates an example of images obtained in steps S1101 to S1105. FIGS. 8A to 8C illustrate the distribution of the oxygen extraction fraction in the brain, calculated by using the QSM method; FIG. 8A shows the susceptibility distribution calculated by the physical property distribution calculator 331, FIG. 8B shows the susceptibility distribution in veins calculated by the tissue separator 332, and FIG. 8C shows the distribution of the oxygen extraction fraction finally obtained.

[Display Image: S1004]

The oxygen extraction fraction distribution calculated by the oxygen extraction fraction distribution calculator 330 and the susceptibility distribution can be displayed on the display 110 (FIG. 2). Alternatively, they may be stored as image data in the external storage device 111, and the image data may be displayed on a desired display device. A mode of the display is not particularly limited, and for example, the oxygen extraction fraction distribution may be displayed in the form of contour lines or a color map as shown in FIG. 8C.

According to the MRI apparatus (or the processing unit) and the image processing method of the present embodiment, the oxygen extraction fraction distribution in the brain including brain parenchyma can be calculated by a simple processing without an impact such as caffeine administration, and therefore, diagnostic accuracy can be enhanced. According to the present embodiment, the susceptibility distribution having a linear relationship with the oxygen extraction fraction is used, and a tissue that allows highly accurate calculation of magnetic susceptibility, for example a vein, is separated to create the separated tissue image, so as to estimate the oxygen extraction fraction. Therefore, it is possible to calculate the oxygen extraction fraction distribution with a high degree of accuracy.

According to the partial volume effect correction, as for the tissue containing a capillary in a size smaller than the pixel size, an error due to the partial volume effect can be reduced, and a degree of accuracy of the calculated oxygen extraction fraction distribution can be improved.

Second Embodiment

In the first embodiment, an example has been described where the susceptibility distribution is used as the physical property that reflects the oxygen extraction fraction. In the present embodiment, as the physical property distribution reflecting the oxygen extraction fraction, a distribution of apparent transverse relaxation rate ($R_2^*$) is calculated.

Also in the present embodiment, the configurations of the computer 109 and of the oxygen extraction fraction calculator 330 are the same as the first embodiment. However, the measurement controller 310 performs control for measuring echoes at a plurality of echo times, at least two, and for acquiring a plurality of complex images at different echo times. Processing details of the physical property distribution calculator 331 and of the oxygen extraction fraction converter 333 are different. Specifically, the physical property distribution calculator 331 calculates the distribution of $R_2^*$ from the complex images obtained at the plurality of echo times, and the oxygen extraction fraction converter 333 converts each pixel value of the distribution of $R_2^*$ into the oxygen extraction fraction. In the present embodiment, the physical property distribution calculator 331 in FIG. 3 shall be read as the $R_2^*$ distribution calculator.

Figure 9:
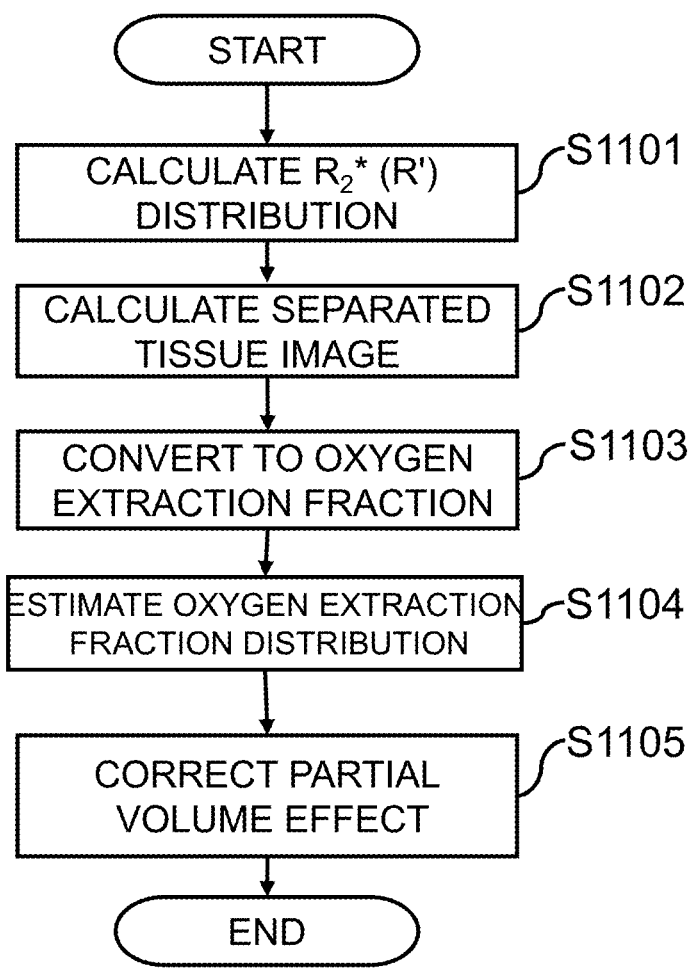
FIG. 9 is a flowchart of the process for calculating the distribution of the oxygen extraction fraction according to a second embodiment.

Focusing on the points different from the first embodiment, with reference to the flowchart of FIG. 9, there will now be described the computer 109 of the present embodiment, mainly the operation of the oxygen extraction fraction calculator 330. In the following description, the functional block diagram of FIG. 3 together with FIG. 4, used in the first embodiment, will be referred to as appropriate.

[Measurement and Image Reconstruction: S1001, S1002]

The measurement controller 310 controls the measuring unit based on the GrE-type pulse sequence as shown in FIG. 5, and measures echoes at a plurality of echo times (TEs). FIG. 5 shows a multi-echo sequence for measuring a plurality of echoes at different TEs after one-time excitation. Alternatively, imaging that uses a sequence for measuring one echo may be executed a plurality of times at various TEs. The image reconstructor 320 reconstructs complex images from the echoes at different TEs.

[Calculate Oxygen Extraction Fraction Distribution: S1003]

[Calculate $R_2^*$ Distribution: S1101]

The $R_2^*$ distribution calculator 331 calculates the distribution of $R_2^*$ from the complex image I(TE) measured at the echo time (TE). Hereinafter, a method for calculating the distribution of $R_2^*$ from the complex image I(TE) will be described.

The complex image I is an image including intensity information and phase information. In this example, attenuation of signals caused by tissue susceptibility variation is calculated, by using an image having intensity information (magnitude image). Formula 10 expresses the signal intensity I(TE) at the echo time TE:

[Formula 10]

$$I(TE)=M_0 \exp(R_2^* \cdot TE) \quad (10)$$

where the proton density within the pixel is $M_0$ and the apparent transverse relaxation rate is $R_2^*$.

The values of each pixel in the plurality of images at different TEs measured by the GrE method, are subjected to the least squares fitting to the signal model as expressed in the formula 10, thereby calculating a distribution of the proton density $M_0$ and a distribution of the apparent transverse relaxation rate $R_2^*$. Since the number of unknowns is two in formula 10, two or more images at different TE are sufficient for the calculation. However, by increasing the number of images (echo numbers), fitting accuracy can be enhanced.

[Calculate Separated Tissue Image: S1102]

The tissue separator 332 calculates separated tissue images from thus calculated $R_2^*$ distribution, being separated into at least two or more living tissues. In this example, a venous region is extracted from the $R_2^*$ distribution, and the $R_2^*$ distribution in veins is separated from the other $R_2^*$ distribution. A method for extracting the $R_2^*$ distribution in veins is the same as the first embodiment, and it is possible to employ, for example, a process using the morphology filter bank (FIG. 7) and a process for differentiating the vein according to the local mean value and the standard deviation.

[Conversion to Oxygen Extraction Fraction: S1103]

The oxygen extraction fraction converter 333 converts each pixel value ($R_2^*$ value) of the $R_2^*$ distribution in veins separated in S1102 into the oxygen extraction fraction. It is known that the $R_2^*$ value in veins is proportional to the concentration of deoxyhemoglobin, i.e., the oxygen extraction fraction (Xiang He et al., "Quantitative BOLD: Mapping of Human Cerebral Deoxygenated Blood Volume and Oxygen Extraction Fraction: Default State", Magnetic Resonance in Medicine, 2007, vol. 57, see Expressions 1 and 2 in pp. 115-126). The oxygen extraction fraction OEF is expressed by formula 11 as the following:

[Formula 11]

$$OEF = \frac{3(R_2^* - R_2)}{4\pi\gamma B_0 \Delta\chi_{do} Hct} \quad (11)$$

where the venous transverse relaxation rate is $R_2$, hematocrit (a numeric value indicating the volume percentage of blood cells in blood) is Hct, and an arteriovenous difference of susceptibility per hematocrit is $\Delta\chi do$.

In formula 11, $\gamma$ represents the nuclear gyromagnetic ratio, and $B_0$ represents magnetic field intensity. Furthermore, as described above, standard values of the hematocrit value and the arteriovenous difference of susceptibility are already known. Alternatively, another examination can be conducted separately and those values may be measured in advance. In veins, $R_2$ is significantly small and it may be ignorable, relative to $R_2^*$ value, the approximate formula 12 may substitute for the formula 11 in the present embodiment, thereby converting the $R_2^*$ value in veins into the oxygen extraction fraction OEF.

[Formula 12]

$$OEF = \frac{3R_2^*}{4\pi\gamma B_0 \Delta\chi_{do} Hct} \quad (12)$$

Processing after the conversion to the oxygen extraction fraction, that is, estimation of the oxygen extraction fraction distribution (S1104) and the partial volume effect correction (S1105) are performed in the same manner as the first embodiment.

According to the procedures as described above, the oxygen extraction fraction in the brain parenchyma can be calculated from the apparent transverse relaxation rate $R_2^*$. Also in this case, the oxygen extraction fraction distribution as shown in FIG. 8C can be obtained, and it may be displayed in any mode on the display 110 as appropriate.

According to the present embodiment, similar to the first embodiment, the oxygen extraction fraction is calculated by performing the image separation of tissue that allows accurate calculation of the oxygen extraction fraction. Therefore, it is possible to obtain the oxygen extraction fraction distribution, non-invasively and accurately. Further according to the present embodiment, the apparent transverse relaxation rate $R_2^*$ is used as a characteristic value, and this allows obtainment of more microscopic structural information relative to the susceptibility distribution, enabling accuracy enhancement in the tissue separation. As a result, it is possible to enhance the accuracy in calculating the oxygen extraction fraction distribution.

The modification examples as described in the first embodiment, may also be applied to the present embodiment, such as employing another tissue separation methods except the morphology filter bank, changing the order of steps as shown in FIG. 4, and skipping the step of the partial volume effect correction, for instance.

Modification Example of the Second Embodiment

In the embodiments above, the oxygen extraction fraction is calculated assuming the real transverse relaxation rate $R_2$ as small enough to be ignored with respect to $R_2^*$ value. However, as seen from the formula 11, it is $R'(=R_2^*-R_2)$ that is in linear relationship with the oxygen extraction fraction. In the present modification example, the measurement controller 310 uses the pulse sequence that can obtain $R_2$, in addition to the pulse sequence of FIG. 5, thereby acquiring a plurality of spin echoes (SE) at different TEs, and obtaining an R' distribution as the physical property.

Figure 10:
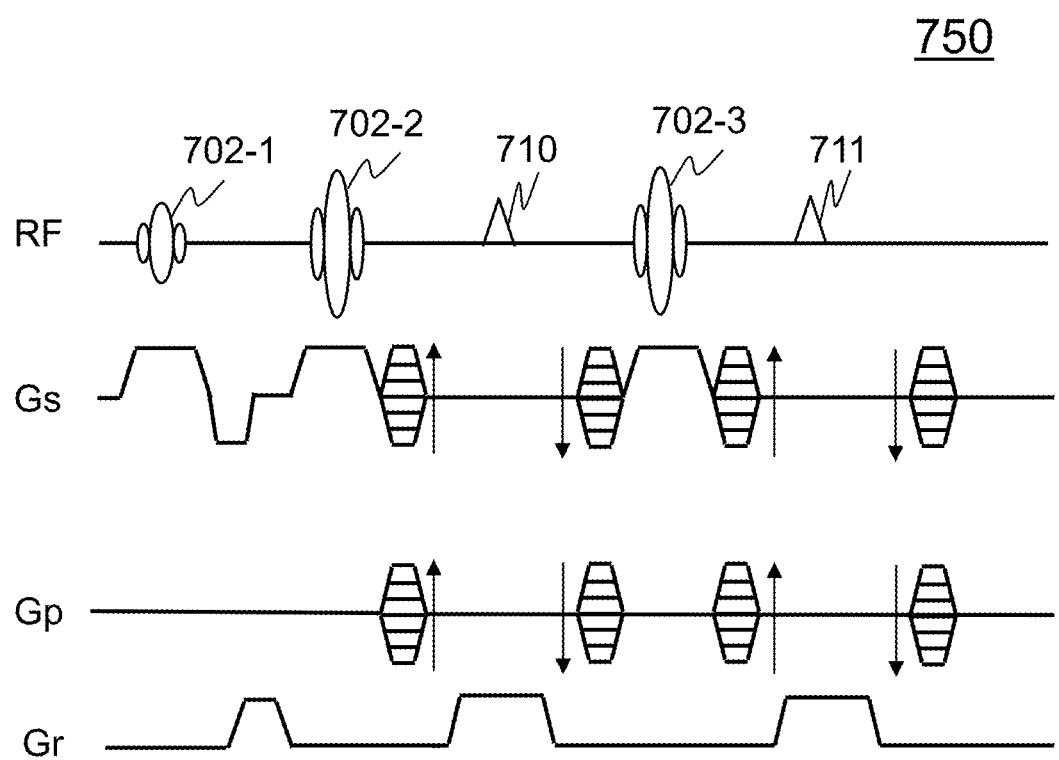
FIG. 10 illustrates one example of the pulse sequence employed in the second embodiment.

As shown in FIG. 10, for example, the Multi-echo SE sequence 750 to which inversion pulses 702-2 and 702-3 are added, can be used as the pulse sequence for obtaining $R_2$. Detailed description of this sequence will not be provided, but according to this sequence, a plurality of echoes at different TEs 710 and 711 can be obtained, as in the case of the GrE sequence shown in FIG. 5. Those echoes are spin echoes not affected by inhomogeneity in the static magnetic field, and by repeating the sequence of FIG. 10, in the slice direction and in the phase encoding direction, with varying the amount of encoding in the respective directions, thereby obtaining a plurality of data items used for SE images (k-space data). The image reconstructor 320 reconstructs those data items into images, and a plurality of SE images with different TEs can be obtained.

The oxygen extraction fraction calculator 330 uses a signal attenuation formula similar to the formula 10, to calculate $R_2$ from the plurality of SE images (calculation of the physical property distribution). Then, by using $R_2^*$ calculated from the GrE image and $R_2$ calculated from the SE image, the oxygen extraction fraction OEF can be calculated according to the formula 11 (conversion to the oxygen extraction fraction). According to the present modification example, though the time required in the measuring step becomes longer (FIG. 3: S1001), more accurate OEF can be calculated. It is alternatively possible to calculate $R_2^*$ and $R_2$, by using a different pulse sequence. For example, $R_2^*$ may be calculated from a plurality of images measured by the 2D GrE-EPI sequence with varying the TE two or more times, and $R_2$ may also be calculated from a plurality of images measured by the 2D SE-EPI sequence with varying the TE two or more times. With the use of the EPI-type sequences as described above, the time required in the measuring step (FIG. 3: S1001) can be reduced.

Third Embodiment

In the present embodiment, similar to the second embodiment, the physical property distribution calculator 331 calculate the apparent transverse relaxation rate $R_2$* as a characteristic reflecting the oxygen extraction fraction. However, the processing performed by the tissue separator 332 (FIG. 3) is different from the second embodiment, and in the present embodiment, the apparent transverse relaxation rate $R_2$* is separated into $R_2$* of brain parenchyma and $R_2$* of the other tissues.

There will now be described the processing of the oxygen extraction fraction distribution calculator 330 of the present embodiment, focusing on the points different from the second embodiment. FIG. 11 is a flowchart showing the processing of the present embodiment. In FIG. 11, the steps with identical details are labeled with the same reference numbers as the steps in FIG. 9, and detailed descriptions will not be provided redundantly.

[Calculate $R_2$* Distribution (R' Distribution): S1101]

Similar to the calculation of $R_2$* distribution (R' distribution) in step S1101 of the second embodiment, the physical property calculator ($R_2$* distribution calculator) 331 uses the intensity information of a plurality of images at different TEs to calculate the apparent transverse relaxation rate $R_2$* on a pixel by pixel basis, whereby the $R_2$* distribution can be obtained. In the measurement, when only the GrE-type pulse sequence is used, the $R_2$* distribution can be obtained, but when the SE-type pulse sequence is used together as described in the modification example of the second embodiment, a distribution of $R'(=R_2*-R_2)$ can be obtained. Hereinafter, the case where the $R_2$* distribution is obtained will be described, representing the $R_2$* distribution and the R' distribution.

[Calculate the Separated Tissue Image: S1102]

The tissue separator 332 extracts a region of veins from the $R_2$* distribution, and calculates the $R_2$* distribution in veins. The method for extracting the $R_2$* distribution in veins is the same as the first embodiment, and there are employed a method, for example, of extracting a linear structure from the $R_2$* distribution, using the morphology filter bank, and a method of extracting the distribution from a magnitude image. Next, based on a difference between the original $R_2$* distribution and the $R_2$* distribution in veins, the $R_2$* distribution of brain parenchyma (referred to as a differential $R_2$* distribution) is calculated.

[Correct Characteristic Value: S1102-1]

The processing here corrects an influence of a substance that varies $R_2$* of brain parenchyma. Byway of example, if there is a deposition of iron protein such as Ferritin in the brain, the value of $R_2$* at the point of deposition indicates a high value. Such an abnormal value of $R_2$* should be detected and eliminated. Specifically, a small area made up a plurality of pixels is set on the differential $R_2$* distribution, a mean value and a standard deviation of $R_2$* in this small area are calculated, and a pixel value exceeding the range of "mean value+N×standard deviation" is extracted as the value of $R_2$* of the tissue with Ferritin deposition. Next, thus extracted $R_2$* is subtracted from the differential $R_2$* distribution, and the result is considered as the corrected $R_2$* distribution in brain parenchyma.

This processing may be performed only on the subject suspected to have Ferritin deposition, or this processing may be skipped. In the separated tissue image calculation step S1102, similar to the first embodiment, in extracting the $R_2$* distribution in veins, the top-hat transformation is performed according to multiple linear structuring elements obtained by three-dimensional change of the angle of the linear structuring element, and a particulate component is separated. After calculating the $R_2$* distribution in the particulate component, it is subtracted from the original $R_2$* distribution, thereby eliminating the tissue with Ferritin deposition mentioned above.

The rest of the procedures, conversion to the oxygen extraction fraction (S1103), estimation of the oxygen extraction fraction distribution (S1104), and the partial volume effect correction (S1105), are performed in the similar matter as the second embodiment.

According to the present embodiment, the $R_2$* distribution in brain parenchyma is subjected to the tissue separation, where the brain parenchyma is a target for obtaining the oxygen extraction fraction, and the oxygen extraction fraction is calculated from thus separated tissue image. This method is very straightforward, thus allowing obtainment of the oxygen extraction fraction with a high degree of accuracy.

Modification Example of the Third Embodiment

In the embodiment above, a value extracted as $R_2$* of the tissue with Ferritin deposition is subtracted from the differential $R_2$*distribution obtained in step S1102 for calculating the separated tissue image, and the result is considered as the $R_2$* distribution in brain parenchyma. In the present modification example, by using the $R_2$* distribution extracted as $R_2$* of the tissue with Ferritin deposition, a binary mask is created, and this binary mask is used in the rest of the calculation procedure.

Specifically, the binary mask is created where $R_2$* of the tissue with Ferritin deposition is 0 and $R_2$* of the other tissues is 1. In the following oxygen extraction fraction conversion (S1103), only the area not covered by the mask (the area where the mask value is 1) is subjected to the oxygen extraction fraction conversion. Similar to the aforementioned embodiments, the area not covered by the mask may be subjected to the estimation of oxygen extraction fraction distribution (S1104), using the separated tissue image (oxygen extraction fraction image) after converted to the oxygen extraction fraction, and further, the partial volume effect correction may be performed thereon.

There have been described embodiments and modification examples of the present invention, but those embodiments may embrace a configuration including an element not referred to, or a configuration excluding an element not necessary. In the above description, there have been described examples of the functions mainly of the computer 109 in the MRI apparatus. However, the functions of the computer 109 may be implemented by an image processor that is independent of the MRI apparatus, as far as the image processor is capable of capturing image data acquired by the MRI apparatus, wirelessly or by wire, or via a portable medium, and the like, and the present invention also embraces this type of image processor.

DESCRIPTION OF SYMBOLS

100: MRI apparatus, 101: subject, 102: static magnetic field coil, 103: gradient coil, 104: shim coil, 105: transmitter coil, 106: receiver coil, 107: transmitter, 108: receiver, 109: computer, 110: display, 111: external storage device, 112: gradient magnetic field power supply, 113: shim power supply, 114: sequence controller, 115: input device, 120: MRI apparatus, 130: MRI apparatus, 310: measurement controller, 320: image reconstructor, 330: oxygen extraction fraction distribution calculator, 331: physical property distribution calculator (susceptibility distribution calculator, $R_2^*$ distribution calculator), 332: tissue separator, 333: oxygen extraction fraction converter, 334: oxygen extraction fraction distribution estimator, 335: partial volume effect corrector

What is claimed is:

1. A magnetic resonance imaging apparatus comprising,
    a measuring unit having a transmitter configured to transmit an RF magnetic field pulse to a subject placed in a static magnetic field, a receiver configured to receive a nuclear magnetic resonance signal generated from the subject, and a gradient magnetic field generator configured to provide the static magnetic field with a gradient magnetic field,
    a measurement controller configured to control an operation of the measuring unit, according to an imaging sequence being preset, and
    a computer configured to perform computation on the nuclear magnetic resonance signal being received, wherein,
    the computer comprises,
    an image reconstructor configured to generate a complex image from the nuclear magnetic resonance signal acquired at least one echo time,
    a physical property distribution calculator configured to calculate a physical property image, having as a pixel value, a physical property reflecting oxygen content characteristics,
    a tissue separator configured to separate the physical property image of a target area into tissue-specific physical property images of at least two types of tissue, and to calculate separated tissue images,
    an oxygen content characteristics converter configured to convert the physical property of each pixel into the oxygen content characteristics, as to at least one of the separated tissue images, and
    an oxygen content characteristics distribution estimator configured to estimate a distribution of the oxygen content characteristics in the target area, based on a condition that a value of any pixel is equal to a mean value of surrounding pixels, in the separated tissue image after converting the pixel value into the oxygen content characteristics.

2. The magnetic resonance imaging apparatus according to claim 1, wherein,
    the physical property distribution calculator comprises a susceptibility distribution calculator configured to calculate a susceptibility distribution from phase information of the complex image.

3. The magnetic resonance imaging apparatus according to claim 1, wherein,
    the measurement controller controls the measuring unit by using an imaging sequence for acquiring nuclear magnetic resonance signals at different echo times at least two, and
    the physical property distribution calculator comprises an $R_2^*$ distribution calculator configured to calculate a distribution of an apparent transverse relaxation rate $R_2^*$, from intensity information of the complex images acquired at multiple different echo times.

4. The magnetic resonance imaging apparatus according to claim 1, wherein,
    the tissue separator separates veins from the other tissues.

5. The magnetic resonance imaging apparatus according to claim 4, wherein,
    the oxygen content characteristics distribution estimator configured to estimate the distribution of the oxygen content characteristics in the target area, on the basis of a first condition that a value of any selected pixel indicating the oxygen content characteristics of a brain tissue is substantially equal to a mean value of pixels surrounding the selected pixel, and a second condition that the mean value of pixels surrounding the selected pixel indicating the oxygen content characteristics of the brain tissue is substantially equal to a mean value of pixels surrounding the selected pixel indicating the oxygen content characteristics of veins.

6. The magnetic resonance imaging apparatus according to claim 1, wherein,
    the tissue separator separates brain parenchyma from the other tissues.

7. The magnetic resonance imaging apparatus according to claim 1, wherein,
    the oxygen content characteristics distribution estimator comprises a partial volume effect corrector configured to correct a partial volume effect, on the basis of the condition that the oxygen content characteristics of any tissue is substantially equal to a mean value of the oxygen content characteristics of a whole brain.

8. The magnetic resonance imaging apparatus according to claim 1, wherein,
    the oxygen content characteristics estimated by the oxygen content characteristics distribution estimator includes any of an oxygen extraction fraction, oxygen saturation, and a metabolic rate of oxygen.

9. The magnetic resonance imaging apparatus according to claim 1, wherein,
    the tissue separator separates an image of any selected tissue, by using a morphology filter that separates an original image into a particulate component image, a vascular component image, and a smoothed image.

10. A method of calculating an oxygen extraction fraction in a test subject by using measurement data acquired by imaging through an MRI apparatus, comprising,
    reconstructing an image from a complex image of the test subject by using the measurement data,
    calculating a susceptibility distribution by using the complex image,
    separating the susceptibility distribution into tissue-specific susceptibility distributions of a plurality of tissues to obtain separated tissue images, and
    estimating the oxygen extraction fraction in the test subject from the tissue-specific susceptibility distributions, as to at least one of the separated tissue images, under the assumption that a magnetic susceptibility of any pixel is equal to the magnetic susceptibility in an area having a predetermined size surrounding the pixel.

11. The method of calculating the oxygen extraction fraction according to claim 10, wherein,
    the oxygen extraction fraction estimated from the separated tissue image is further subjected to a partial volume effect correction, based on a condition that the oxygen extraction fraction in any tissue is substantially equal to a mean value of the oxygen extraction fraction in a whole brain.

12. The method according to either claim 10,
the plurality of tissues includes brain veins and brain parenchyma.

13. A method of calculating an oxygen extraction fraction in a test subject by using measurement data acquired by imaging through an MRI apparatus, comprising,
reconstructing a plurality of complex images at different echo times by using the measurement data,
calculating a distribution of an apparent transverse relaxation rate $R_2^*$ or a distribution of a difference between the apparent transverse relaxation rate $R_2^*$ and a transverse relaxation rate $R_2$,
separating the distribution of the apparent transverse relaxation rate $R_2^*$ or the distribution of the difference, into tissue-specific separated images of a plurality of tissues, and
estimating the oxygen extraction fraction in the test subject, from the distribution of the apparent transverse relaxation rate $R_2^*$ or the distribution of the difference, as to at least one of the separated tissue images, under the assumption that a value of any selected pixel is equal to pixel values in an area having a predetermined size surrounding the selected pixel.

* * * * *